(12) United States Patent
Plachetka et al.

(10) Patent No.: US 9,265,732 B2
(45) Date of Patent: Feb. 23, 2016

(54) DOSAGE FORMS FOR ADMINISTERING COMBINATIONS OF DRUGS

(75) Inventors: John Plachetka, Chapel Hill, NC (US); Donna Gilbert, Chapel Hill, NC (US)

(73) Assignee: Pozen Inc., Chapel Hill, NC (US)

( * ) Notice: Subject to any disclaimer, the term of this patent is extended or adjusted under 35 U.S.C. 154(b) by 2040 days.

(21) Appl. No.: 11/987,970

(22) Filed: Dec. 6, 2007

(65) Prior Publication Data

US 2008/0175897 A1 Jul. 24, 2008

Related U.S. Application Data

(63) Continuation-in-part of application No. 11/712,969, filed on Mar. 2, 2007, now abandoned.

(60) Provisional application No. 60/779,373, filed on Mar. 6, 2006.

(51) Int. Cl.

| *A61K 9/48* | (2006.01) |
| *A61K 9/24* | (2006.01) |
| *A61K 31/404* | (2006.01) |
| *A61K 9/20* | (2006.01) |
| *A61K 9/28* | (2006.01) |
| *A61K 31/485* | (2006.01) |
| *A61K 31/542* | (2006.01) |
| *A61K 45/06* | (2006.01) |

(52) U.S. Cl.
CPC .............. *A61K 9/209* (2013.01); *A61K 9/2054* (2013.01); *A61K 9/2077* (2013.01); *A61K 9/2846* (2013.01); *A61K 9/2866* (2013.01); *A61K 31/485* (2013.01); *A61K 31/542* (2013.01); *A61K 45/06* (2013.01)

(58) Field of Classification Search
None
See application file for complete search history.

(56) References Cited

U.S. PATENT DOCUMENTS

| 4,503,031 | A | * | 3/1985 | Glassman | ............... 424/467 |
| 4,844,907 | A | * | 7/1989 | Elger et al. | ............... 424/465 |
| 5,624,677 | A | | 4/1997 | El-Rashidy | |
| 5,872,145 | A | | 2/1999 | Plachetka | |
| 6,060,499 | A | | 5/2000 | Plachetka | |
| 6,077,539 | A | | 6/2000 | Plachetka | |
| 6,143,278 | A | | 11/2000 | Elkhoury | |
| 6,451,806 | B2 | | 9/2002 | Farrar | |
| 6,479,551 | B1 | | 11/2002 | Plachetka | |
| 6,495,535 | B1 | | 12/2002 | Plachetka | |
| 6,586,458 | B1 | | 7/2003 | Plachetka | |
| 6,685,964 | B1 | * | 2/2004 | Bartholomaeus et al. | .... 424/489 |
| 6,926,907 | B2 | | 8/2005 | Plachetka | |
| 7,030,162 | B2 | | 4/2006 | Plachetka | |
| 7,060,694 | B2 | | 6/2006 | Plachetka | |
| 7,332,183 | B2 | | 2/2008 | Plachetka | |
| 2003/0069255 | A1 | * | 4/2003 | Plachetka | ............... 514/255.04 |
| 2003/0232876 | A1 | | 12/2003 | Plachetka | |
| 2004/0180089 | A1 | | 9/2004 | Plachetka | |
| 2004/0247677 | A1 | | 12/2004 | Oury | |
| 2005/0019398 | A1 | | 1/2005 | Kotharl et al. | |
| 2005/0249811 | A1 | | 11/2005 | Plachetka | |
| 2007/0122470 | A1 | | 5/2007 | Johansson et al. | |
| 2007/0275059 | A1 | | 11/2007 | Kotharl et al. | |
| 2010/0062064 | A1 | | 3/2010 | Ault et al. | |
| 2010/0172983 | A1 | | 7/2010 | Plachetka | |

FOREIGN PATENT DOCUMENTS

| EP | 1 068 867 A2 | 1/2001 |
| WO | WO 2006/081347 | 8/2006 |
| WO | WO 2009/145905 A1 | 12/2009 |

OTHER PUBLICATIONS

International Preliminary Report on Patentability for PCT/US2007/005266 filed Mar. 2, 2007.
International Search Report for PCT/US 2007/05266 filed Mar. 2, 2007.
Written Opinion of the International Searching Authority for PCT/US 2007/05266 filed Mar. 2, 2007.
Crighton, et al., "A Comparison of the Effects of Intravenous Tramadol, Codeine, and Morphine on Gastric Emptying in Human Volunteers," *Anesth. Analg.* 87:445-449 (1998).
Seaber, et al., "The Novel Anti-Migraine Compound Zolmitriptan (Zomig 311C90) has no Clinically Significant Interactions with Paracetamol or Metoclopramide," *Eur. J. Clin. Pharm.* 53:229-234 (1997).
Office Action issued in corresponding Eurasian Patent Application No. 200870325/28, received on Aug. 23, 2011.

* cited by examiner

*Primary Examiner* — Tigabu Kassa
(74) *Attorney, Agent, or Firm* — Parker Highlander PLLC

(57) ABSTRACT

The present invention is directed to dosage forms that can be used in therapeutic methods involving the oral co-administration of a combination of at least two drugs, one of which impairs gastrointestinal absorption and one of which does not. The dosage forms are designed so that the drug impairing absorption is not released into the gastrointestinal tract of a patient until after the drugs that do not impair absorption have been released and substantially absorbed. The invention may be used in treatment of migraine using a combination of triptans and NSAIDs or in the treatment of pain using a combination of NSAIDs and opioid analgesics.

21 Claims, 3 Drawing Sheets

DOSAGE FORMS FOR ADMINISTERING COMBINATIONS OF DRUGS

CROSS REFERENCE TO RELATED APPLICATIONS

The present application is a continuation-in-part of U.S. application Ser. No. 11/712,969, filed on Mar. 2, 2007, which claims priority to, and the benefit of, U.S. provisional application 60/779,373 filed on Mar. 6, 2006. The contents of these previous applications are hereby incorporated by reference in their entirety.

FIELD OF THE INVENTION

The present invention is directed to dosage forms for orally co-administering drugs in cases in which at least one drug, as an unintended consequence of its use, impairs absorption from the gastrointestinal tract of patients, and at least one other drug that does not. The dosage forms delay the release of the absorption-impairing drug until after the non-absorption impairing drug has been at least partially absorbed. Thus, the speed and efficiency of overall delivery is enhanced. The dosage forms will be of particular value for pharmaceutical compositions in which certain non-narcotic analgesics are combined with triptans or opioid analgesics.

BACKGROUND OF THE INVENTION

Therapeutic methods involving the co-administration of drugs may be used in cases where larger doses of a single agent would not have a therapeutic benefit or would result in unacceptable toxicity or side effects, or where multiple mechanisms of action may be beneficial. This approach is commonly used in the treatment of pain, viral or bacterial infection, asthma, hypertension and cancer. For example, opioid analgesics may be combined with other analgesics such as acetaminophen or non-steroidal anti-inflammatory drugs (NSAIDs, see generally, U.S. Pat. No. 6,451,806). Similarly, in the field of migraine therapeutics, it has been reported that the co-administration of triptans together with NSAIDs results in better overall relief than the administration of either agent alone (U.S. Pat. No. 6,586,458).

Unfortunately, there are instances in which one drug in a combination, due to an unwanted pharmacological effect on the gastrointestinal tract, impairs the absorption of other drugs from a patient's gastrointestinal tract. This appears to be true both for drug combinations involving the use of opioids (Crighton, et al., *Anesth. Analg.* 87:445-449 (1998)), and for those involving the use of triptans (Seaber, et al., *Eur. J. Clin. Pharm.* 53:229-234 (1997)). Impaired absorption of one component in such combinations can lead to a delayed onset of action for this component and to a less than optimal overall therapeutic effect.

A number of approaches have been taken in an attempt to compensate for poor absorption of drugs from the gastrointestinal tract of patients. These have included the co-administration of an agent that enhances absorption (U.S. Pat. No. 5,968,972) or that increases gastric motility (U.S. Pat. No. 6,479,551). Alternatively, drugs can be administered by a route that avoids a patient's gastrointestinal tract, e.g., using transmucosal or transdermal delivery (U.S. Pat. No. 5,624,677; U.S. Pat. No. 6,143,278). While these methods may be useful for certain therapies, alternative approaches would be desirable.

SUMMARY OF THE INVENTION

The present invention is directed to dosage forms for pharmaceutical compositions containing at least two drugs; one that impairs absorption from a patient's gastrointestinal tract as an unintended consequence of its therapeutic use, and one that does not. By designing dosage forms so that the release of the absorption-impairing drug is delayed until after the non-impairing drug has been at least partially absorbed, a more rapid and/or an improved overall therapeutic effect can be achieved. The invention should be of value in the treatment of migraine headache using a combination of an absorption-impairing triptan and a non-absorption impairing NSAID. It should also be of value for combinations involving opioid analgesics and other drugs such as non-narcotic analgesics.

In its first aspect, the invention is directed to a pharmaceutical composition in unit dosage form for oral administration to a patient. The composition contains at least two different drugs: a first drug that provides a therapeutic benefit but unintentionally impairs other therapeutic agents from being absorbed from a patient's gastrointestinal tract, and a second drug that provides a therapeutic benefit but does not impair absorption of other therapeutic agents. Both of these drugs should be present in a therapeutically effective amount, i.e., upon ingestion of one or more unit dosage forms by a patient, sufficient drug should be present to achieve the desired therapeutic effect.

For example, a therapeutically effective amount of an analgesic drug or an NSAID analgesic drug would be a dosage sufficient to reduce pain, or the swelling and pain associated with inflammation. Similarly, a therapeutically effective dose of a drug administered to treat migraine, would be an amount sufficient to reduce the pain or other symptoms associated with a migraine attack. Also, it will be understood that, for the purposes of the present invention, any pharmaceutically acceptable form of a drug may be used including, but not limited to, hydrochlorides, hydrobromides; benzoates; mesylates; phosphates; succinates; and malates. Unless otherwise indicated, reference made herein to a drug such as a triptan, NSAID, analgesic, opioid analgesic etc., will be understood to encompass all of these and similar pharmaceutically acceptable forms of the drugs, especially all pharmaceutically acceptable salts.

The main characteristic of the dosage form of the present invention is that it is designed to deliver the drugs in the pharmaceutical composition in a specific coordinated manner. In particular, upon ingestion by a patient, the second drug, i.e., the drug that does not impair gastrointestinal absorption, is released from the unit dosage form before the first, absorption impairing drug. The timing of delivery is also very important. In general, essentially none of the first drug should be released from the unit dosage form into the gastrointestinal tract of a patient for a period that is equal to or greater than one-fourth Tmax2, where Tmax2 is the time interval necessary to reach a peak plasma concentration of the second, non-absorption impairing, drug when it is administered to a patient in essentially the same dosage form but as the sole active agent. In other words, Tmax2 is the time interval from the ingestion of a tablet containing the second drug alone, until the plasma level of the drug in a patient reaches a maximum. This is a common pharmacokinetic parameter that can be determined using methodology well known in the art and whose values for different drugs are provided in standard reference works such as the Physician's Desk Reference (Medical Economics, Montvale N.J.).

Tmax values typically vary somewhat between people and, as a result, they are sometimes expressed as a range based upon effects observed in many individuals. For the purposes of the present invention, unless otherwise indicated, Tmax will be considered to be the middle of any such range. For example, if Tmax is recognized in the art as being 1-2 hours, for the purposes of the present invention it would be considered to be 90 minutes and ¼ Tmax would be about 22 minutes. Thus, the phrase "period that is equal to or greater than one-fourth Tmax2" would mean 22 minutes or longer. For dosage forms in which, an NSAID or other non-narcotic analgesic is present as the non-absorption impairing component, the release of the absorption impairing drug should be delayed for a minimum of 10 minutes, and more preferably the delay should be for a minimum of 20, 30 or 60 minutes. Unless otherwise indicated by context, the term "is released" means the time when a substantial portion of a drug (e.g., greater than 1%) is discharged from a dosage form and enters into the gastrointestinal tract of a patient.

In a preferred embodiment, the pharmaceutical composition described above is in the form of a multilayer tablet, preferably where essentially all of the first, absorption-impairing, drug is surrounded by a membrane that does not release it, or which is formulated with components that delay its release, for a time period at least equivalent to one-fourth Tmax2 and, preferably, for a period of at least one-half Tmax2. The term "essentially all" as used herein refers to greater than 90% of the total amount of the drug in a unit dosage form, preferably more than 95%, and still more preferably to more than 99%. The term "essentially none" refers to less than 10% of the total amount of drug in a dosage form, preferably less than 5% and more preferably less than 1%.

In one preferred embodiment, essentially all of the first drug is found in a single core layer of a tablet surrounded by a membrane described above and essentially all of the second drug is located in one or more layers outside of this core. Alternatively, an agent that delays drug release, may be mixed in with the absorption impairing drug. The release delaying agent should typically be present in compositions in a range of between 10% and 70% by weight and will constitute either a polymeric substance which swells and/or a gel. Examples of appropriate agents are: hydroxypropylmethylcellulose; crosslinked polyvinylpyrrolidone; crosslinked sodium carboxymethylcellulose; carboxyvinyl polymers; polyvinyl alcohols and derivatives thereof including derivatives of ethylcellulose, methylcellulose and cellulose. Of these, the most preferred is hydroxypropylmethylcellulose.

In an alternative embodiment, the dosage form may be a capsule, preferably in which essentially all of the first drug is located in one or more particles surrounded by a membrane that does not release this drug or is formulated with components that delays release for a period of at least ½ Tmax2 and preferably for a period of at least Tmax2. Generally, the capsules will contain multiple particles of the membrane-surrounded first drug with essentially all of the second drug being located outside of these particles.

Among the preferred absorption-impairing drugs for use in the dosage forms are the triptans, e.g., sumatriptan, eletriptan, rizatriptan, frovatriptan, almotriptan, zolmitriptan and naratriptan. The most preferred of these is sumatriptan present in dosage forms in an amount of between 25 and 100 mg, together with a non-narcotic analgesic, such as acetaminophen or an NSAID, such as naproxen or naproxen sodium at 200-600 mg. When naproxen is used, membranes should be designed so that essentially no triptan is released for a period of at least 45 minutes after the dosage form is ingested by a patient. In the case of naproxen sodium, no triptan should be released for a period of at least 20 minutes. If desired, these same parameters may be used for other combinations of NSAIDs and triptans or for combinations involving opioid analgesics and non-narcotic analgesics. Dosage forms containing triptans and analgesics may be used to treat patients for migraine headache.

There is a second important consideration attached to the use of naproxen sodium in drug combinations. Although this drug does not directly impair absorption of other drugs, it is believed that, due to its relatively poor dissolution characteristics in stomach acid, it has the potential for entrapping other, faster dissolving, drugs (see e.g., published US application 2004-0180089) and to thereby impair their release. This is something that one of skill in the art may want to take into account when making a dosage form for a particular clinical objective. For example, if one wanted the triptan to be released quickly, then keeping it separate from the naproxen sodium (e.g., in a tablet where triptan and NSAID are in a side by side arrangement) would be desirable. If, instead, the objective is to delay the release of triptan until a substantial portion of the naproxen can be absorbed, then putting the triptan in a core surrounded by naproxen would be an acceptable arrangement.

Another group of preferred absorption-impairing drugs for use in the dosage forms are the opioid analgesics, e.g., alfentanil, buprenorphine, butorphanol, codeine, dezocine, dihydrocodeine, fentanyl, hydrocodone, hydromorphone, levorphanol, meperidine, methadone, morphine, nalbuphine, oxycodone, oxymorphone, pentazocine, propiram, propoxyphene, sufentanil and tramadol. Opioid analgesics may be combined with analgesics that do not impair gastrointestinal absorption and administered to patients in a therapeutically effective amount for the treatment of pain.

It will be understood that the dosage forms described above can also be used for compositions having more than one absorption impairing drug and/or more than one non-absorption impairing drug. In these cases, essentially all of the absorption impairing drugs should be contained within one or more membranes that delay their release until after all of the non-absorption impairing drugs have been released. The Tmax used in determining the time of release, i.e., Tmax2 should be that of the non-impairing drug that takes the longest to reach a peak plasma concentration, i.e., the one with the longest Tmax.

In all of the dosage forms described above, disintegrants may be used to facilitate the break up of tablet components after ingestion by a patient. Suitable disintegrants will be known to the person skilled in the art and a non-limiting list of examples includes croscarmellose sodium, crospovidone, sodium starch glycolate, povidone, crosslinked polyvinylpyrrolidone, starch, low substituted hydroxymethylcellulose, methylcellulose, microcrystalline cellulose. Effervescence which results from a reaction of sodium bicarbonate with an acid when added to water can also be an effective way to cause disintegration of a tablet. The acid for this reaction can be provided by the stomach acid, the drug substance, the addition of a salt such as tartaric or citric acid or by other acid containing excipients.

Disintegrants may be included with either the absorption-impairing drug, the non-impairing drug or both. They will be of particular value when added to the non-impairing drug for the purpose of increasing the amount of drug absorbed by a patient prior to the release of the absorption-impairing drug. For example, in a tablet where the non-impairing drug is released immediately and the absorption-impairing drug is released after 20 minutes, more non-impairing drug should be absorbed in the presence of a disintegrant than in its absence.

BRIEF DESCRIPTION OF THE DRAWINGS

FIG. 2.

FIG. 4.

FIG. 5.

DEFINITIONS

A. "Long acting," shall refer a drug having a pharmacokinetic half-life of at least 4 hours, and preferably at least 8-14 hours and a duration of action equal to or exceeding about 6-8 hours. Examples of long acting NSAIDs are: flurbiprofen with a half-life of about 6 hours; naproxen and naproxen sodium with half-lives of about 12 to 15 hours and about 12 to 13 hours respectively; oxaprozin with a half-life of about 42 to 50 hours; etodolac with a half-life of about 7 hours; indomethacin with a half-life of about 4 to 6 hours; ketorolac with a half-life of up to about 8-9 hours; nabumetone with a half-life of about 22 to 30 hours; mefenamic acid with a half-life of up to about 4 hours; and piroxicam with a half-life about of about 4 to 6 hours. If an analgesic or other drug does not naturally have a half life sufficient to be long-acting, it can be made long-acting by the way in which it is formulated. Unless otherwise indicated, reference to a "long-acting" drug shall include drugs specially formulated to be long-acting. Methods for making appropriate long-acting formulations are well known in the art (see e.g., Remington's Pharmaceutical Sciences, 16.sup.th ed., A. Oslo editor, Easton, Pa. (1980); Controlled Drug Delivery, Edith Mathiowitz, John Wiley & Sons (1999), ISBN: 0471148288).

B. "Therapeutically effective amount" as to drug dosage shall mean a dosage that provides the specific pharmacological response for which the drug is administered in a significant number of subjects in need of such treatment. For drugs already on the market, a therapeutically effective amount shall include dosages that have been determined as safe and effective for any indication. Nevertheless, this does not necessarily exclude substantially lesser (or greater) dosages than established minimum (or maximum) dosages in particular cases.

C. "Co-timely" with respect to drug administration means administration of a second drug while a first drug is still present in a therapeutically effective amount.

D. "Coordinated" in the practice of the present invention means administration of drugs in such a manner that effective plasma levels of the non-absorption impairing drug (or drugs) are present in a subject before the absorption-impairing drug is released.

E. "Unit dosage from" shall mean a single drug administration entity. By way of example, a single tablet, or capsule would be a unit dosage form.

DETAILED DESCRIPTION OF THE INVENTION

The present invention is directed to oral dosage forms for the co-administration of at least two drugs, one which impairs gastrointestinal absorption and one which does not. The dosage forms are designed so that the drug impairing absorption is not released until after the non-impairing drug has been released and had an opportunity to be at least partially absorbed.

For convenience, the rate at which the non-impairing drug is absorbed is expressed as Tmax2, which is defined as the time interval between the ingestion of the drug when administered as the sole therapeutic agent, and the time at which the plasma concentration of the drug peaks. Release of the absorption impairing drug should generally be delayed for a period equivalent to, at a minimum, one-fourth Tmax2. One preferred way to delay release is by surrounding the absorption impairing drug with a membrane that degrades or dissolves at a preselected rate. However, other alternatives may also be used. For example, mixing in polymers (e.g., hydroxypropylmethylcellulose) that delay drug release (e.g., by swelling) with a drug such as a triptan or opioid analgesic may be used Making of Pharmaceutical Preparations The pharmaceutical compositions of the invention include tablets and capsules that can be made in accordance with methods that are standard in the art (see, e.g., *Remington's Pharmaceutical Sciences*, 16$^{th}$ ed., A Oslo editor, Easton, Pa. (1980)). Drugs and drug combinations will typically be prepared in admixture with conventional excipients. Suitable carriers include, but are not limited to: water; salt solutions; alcohols; gum arabic; vegetable oils; benzyl alcohols; polyethylene glycols; gelatin; carbohydrates such as lactose, amylose or starch; magnesium stearate; talc; silicic acid; paraffin; perfume oil; fatty acid esters; hydroxymethylcellulose; polyvinyl pyrrolidone; etc. The pharmaceutical preparations can be sterilized and, if desired, mixed with auxiliary agents such as: lubricants, preservatives, disintegrants; stabilizers; wetting agents; emulsifiers; salts; buffers; coloring agents; flavoring agents; or aromatic substances.

Membranes that delay the release of absorption-impairing drugs may be applied to a core or layer containing the drug using standard coating techniques. The coating materials may be dissolved or dispersed in organic or aqueous solvents and may include one or more of the following materials: methacrylic acid copolymers, shellac, hydroxypropylmethcellulose phthalate, polyvinyl acetate phthalate, hydroxypropylmethylcellulose trimellitate, carboxymethylethyl-cellulose, cellulose acetate phthalate, ethylcellulose or other suitable coating polymer(s). The rate at which membranes dissolve can be controlled by the polymer or combination of polymers selected and/or ratio of pendant groups, and may be pH dependent. For example, dissolution characteristics of the polymer film can be altered by the ratio of free carboxyl groups to ester groups. Membranes may also contain pharmaceutically acceptable plasticizers such as triethyl citrate, dibutyl phthalate, triacetin, polyethylene glycols, polysorbates or other plasticizers. Additives such as dispersants, colorants, anti-adhering and anti-foaming agents may also be included. The degree to which a membrane delays drug release can also be controlled by altering the thickness of the membrane. The same polymers may also be mixed with drugs to delay release.

For any given membrane composition, the timing of release can be empirically determined using in vitro experimental techniques that are well known in the art (see e.g., procedures described in the United States Pharmacopeia, see <721> and <724>). For example, the release of a marker substance into a medium mimicking in vivo conditions may be determined for membranes of various thickness. In this manner, a correlation between, for example, thickness and release can be established and used to in constructing a membrane that will release drug at a desired time.

The Making of Tablet Dosage Forms

Preferably, drug combinations will be in the form of a bi- or multi-layer tablet. In a bilayer configuration, one portion of the tablet contains the non-absorption impairing drug (e.g., a non-narcotic analgesic such as an NSAID) in the required dose along with appropriate excipients, agents to aid dissolution, lubricants, fillers, etc. The second portion of the tablet will contain the absorption-impairing drug (e.g., a opioid analgesic or triptan) in the required dose along with other excipients, dissolution agents, lubricants, fillers, etc. The absorption-impairing drug may be surrounded by a membrane which does not dissolve until at least one-fourth Tmax of the non-impairing drug. Alternatively, the release of the absorption-impairing drug can be delayed by mixing this drug with an agent that delays its release, e.g., a polymer that swells when it comes in contact with fluid in the gastrointestinal tract. The amount of polymer to be included may be determined using dissolution tests as described above.

In general, tablets will be designed so that the non-impairing drug is released immediately after ingestion by a patient. However, there may be instances in which, due to instability in a patient's stomach, the drug is inside an enteric coating that does not release it until the drug has reached a patient's intestine. In these cases the value of Tmax2 will correspond to the period between the drug's release and the attainment of a peak plasma concentration, plus the period of time needed for the drug to arrive in the patient's intestine.

Dosage Forms Containing Analgesics in Combination with Triptans or Opioid Analgesics The two most preferred combinations for use in dosage forms are non-narcotic analgesics (particularly NSAIDs, with long acting NSAIDs being preferred) together with either triptans or opioid analgesics. In both cases, the non-narcotic analgesic should be released first, preferably within 5 minutes after ingestion, and the release of triptan or opioid analgesic is delayed for at least 10 minutes after ingestion and preferably for at least 20, 30 or 60 minutes. The triptan/NSAID combinations will be useful primarily in the treatment of migraine and combinations involving opioid analgesics will be useful in treating other types of acute or chronic pain. Guidance concerning the amount of these agents to be used in tablets or capsules and the daily dosage that should be administered to patients is provided in Tables 1-3. All of the agents listed are well known in the art and may be either purchased commercially or manufactured using established methodology. The numbers provided in the tables refer to the active component in drug compounds. However, it will be understood that any pharmaceutically acceptable form of a drug may be used. It will also be understood that the information in the tables is for guidance only. Actual dosages and tablet amounts may be altered by physicians and other medical personnel based upon clinical and practical considerations.

TABLE 1

Dosage Information for Opioid analgesics

| Drug | Approximate Amount per Tablet or Capsule (mg) | Maximum Daily Therapeutic Dose (mg/kg body wt/day) |
|---|---|---|
| Alfentanil | 10-200 mg (preferably 20-100 mg) | 3.0 |
| Buprenorphine | 1-20 mg (preferably 2-10 mg) | .015 |
| Codeine | 5-100 mg (preferably 10-50 mg) | 6.0 |
| Dezocine | 1-200 mg (preferably 10-100 mg) | 0.167 |
| Fentanyl | 0.05-5.0 mg (preferably 0.1-2.0 mg) | .0005 |
| Dihydrocodeine | 10-200 mg (preferably 20-100 mg) | 3.2 |
| Hydrocodone | 1-100 mg (preferably 5-50 mg) | 0.75 |
| Hydromorphone | 1-100 mg (preferably 2-50 mg) | 0.40 |
| Levorphanol | 0.5-50 mg (preferably 1-20 mg) | 0.15 |
| Meperidine | 5-200 mg (preferably 20-150 mg) | 15 |
| Methadone | 1-100 mg (preferably 2-50 mg) | 0.5 |
| Morphine | 5-200 mg (preferably 10-150 mg) | 1.67 |
| Nalbuphine | 1-150 mg (preferably 5-100 mg) | 1.0 |
| Oxycodone | 1-200 mg (preferably 5-100 mg) | 0.333 |
| Oxymorphone | 0.5-100 mg (preferably 1-50 mg) | 0.15 |
| Pentazocine | 1-100 mg (preferably 2-50 mg) | 0.5 |
| Propiram | 10-200 mg (preferably 20-150 mg) | 2.5 |
| Propoxyphene | 10-200 mg (preferably 20-100 mg) | 6.5 |
| Sufentanil | .001-0.1 mg | .025 |
| Tramadol | 10-200 mg (preferably 20-100 mg) | 6.67 |

TABLE 2

Dosing Information for Triptans

| Drug | Approximate Amount per Tablet or Capsule | Maximum Daily Therapeutic Dose |
|---|---|---|
| Sumatriptan | 5-200 mg (preferably 20-100 mg) | 0.2 mg/kg/day |
| Eletriptan | 10-100 mg (preferably 20-40 mg) | approximately 80 mg |
| Rizatriptan | 1-50 mg (preferably 3-15 mg) | 0.5 mg/kg/day |
| Frovatriptan | 1-30 mg (preferably 2-10 mg) | 0.125 mg/kg/day |
| Almotriptan | 1-30 mg (preferably 5-20 mg) | 25 mg |
| Zolmitriptan | 1-30 mg (preferably 2-20 mg) | 10 mg |
| Naratriptan | 0.1-20 mg (preferably 0.5-10 mg) | 0.0833 mg/kg/day |

NSAIDs compatible with the present invention are well known in the art and are either commercially available or can be synthesized using standard techniques of medicinal chemistry. Although the dosage of NSAID may be adjusted by a clinician on a case-by-case basis, general guidelines have been established in the art for many of these compounds.

Examples of NSAIDs (with typical daily doses in parentheses) are as follows: propionic acids (fenoprofen (1500 mg); flurbiprofen (200 mg); suprofen; benoxaprofen; ibuprofen (1600 mg); ketoprofen (200 mg); naproxen (750 mg); oxaprozin (1200 mg)); acetic acids (diclofenac (100 mg); aceclofenac (200 mg); etodolac (1200 mg); indomethacin (75-150 mg); ketorolac (10-30 mg)); ketones (nabumetone (1500 mg); sulindac (300 mg); tolmetin (800 mg)); fenamates (meclofenamate (400 mg); tolfenamic acid (400 mg); mefenamic acid); oxicams (droxicam; piroxicam (20 mg)); lomoxicam (30 mg); meloxicam (15 mg); tenoxicam) salicylates (aspirin; diflunisal); pyrazolinates (oxyphenbutazone; azapropazone; phenylbutazone); COX-2 inhibitors (rofecoxib (50 mg); valdecoxib (20-40 mg); etorocoxib (60-120 mg); celecoxib (200 mg); lumiracoxib (100-200 mg); JTE-522; NS-398; and CS-502).

While the experienced clinician is able to monitor and adjust dosages for each patient relative to the severity of pain and the presence of side effects, approximate maximum daily dosages are as follows: flurbiprofen 300 mg; naproxen 1500 mg; naproxen sodium 1650 mg; oxaprozin 1800 mg; etodolac 1200 mg; indomethacin 150-200 mg; ketorolac 120 mg i.m. and 40 mg when taken orally; nabumetone 2000 mg; mefenamic acid 1000 mg; and piroxicam 20 mg. In particular instances, however, exceeding these "maximum" dosages may be the therapeutic choice of a medical professional.

TABLE 3

Dosing Information for select NSAIDs

| Drug | Approximate Amount per Tablet or Capsule | Maximum Daily Therapeutic Dose |
|---|---|---|
| Ibuprofen | 20-1000 mg (preferably 50-800 mg) | 3200 mg |
| Flurbiprofen | 20-200 mg (preferably 50-100 mg) | 300 mg |
| Ketoprofen | 15-100 mg (preferably 25-75 mg) | 300 mg |
| Naproxen | 100-1000 mg (preferably 200-600 mg) | 1500 mg |
| Oxaprozin | 200-800 mg (preferably 300-600 mg) | 1800 mg |
| Etodolac | 100-600 mg (preferably 200-400 mg) | 1200 mg |
| Ketorolac | 1-100 mg (preferably 5-50 mg) | 40 mg |
| Nabumetone | 300-1000 mg (preferably 400-800 mg) | 2000 mg |
| Mefenamic Acid | 50-500 mg (preferably 200-400 mg) | 1000 mg |
| Indomethacin | 10-100 mg (preferably 20-80 mg) | 200 mg |
| Piroxicam | 5-40 mg (preferably 10-20 mg) | — |
| Celecoxib | 50-400 mg (preferably 100-200 mg) | 400 mg |
| Rofecoxib | 5-100 mg (preferably 10-50 mg) | — |

Use in Therapeutic Methods

The dosage forms described above can be used as an improvement in any existing therapy involving the co-administration of a drug that impairs gastrointestinal absorption together with one or more drugs that do not impair absorption. Thus, the tablets and capsules may be used to replace dosage forms containing one component of the combination or dosage forms which contain both components but in which the release of drugs is not coordinated in the manner described herein. Dosages administered using the tablets and capsules of the present invention should be approximately the same as those given when individual drugs of the combination are separately administered. In the case of combinations involving triptans and non-narcotic analgesics, guidance concerning dosages and the amount present in tablets or capsules may be found in Tables 2 and 3 above. These dosage forms will be used primarily for treating patients with migraine headache and may be taken at the onset of symptoms associated with a migraine attack.

Combinations involving opioid analgesic and non-narcotic analgesics can be used in treating a wide variety of different types of acute or chronic pain, including post-operative pain and pain associated with chronic diseases such as cancer. Guidance concerning dosages and the amount of each drug present in tablets or capsules may be found in Tables 1 and 3. In all cases, sufficient drug should be administered to achieve the intended therapeutic benefit, i.e., relief of pain.

EXAMPLES

Example 1

Triptan and NSAID

Figure 1:
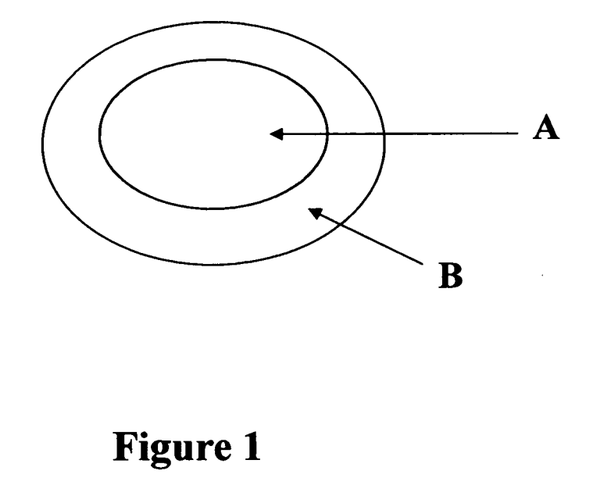
FIG. 1: The figure shows a tablet configuration in which there is a core containing a drug that impairs absorption surrounded by an outer layer containing a drug that does not impair absorption. A: Drug in Core (inner layer); B: Drug in Outer layer

The present example describes a compression-coated or press-coated tablet consisting of sumatriptan succinate in the core and naproxen sodium surrounding the core. Refer to FIG. 1 for schematic of the tablet.

TABLE 4

Composition for Core (40 mg sumatriptan)

| Ingredient | Mg/Tablet |
|---|---|
| Intra-Granular Ingredients | |
| Sumatriptan Succinate, USP[1] | 56.0 |
| Lactose Monohydrate, NF | 56.0 |
| Purified Water, USP[2] | QS |
| Extra-Granular Ingredients | |
| Anhydrous Lactose, NF | 112.0 |
| Microcrystalline Cellulose, NF | 26.2 |
| Croscarmellose Sodium, NF | 2.54 |
| Magnesium Stearate, NF | 1.27 |
| Total | 254.0 |

[1]56.0 mg of sumatriptan succinate is equivalent to 40 mg of sumatriptan
[2]Purified Water, USP is removed during the drying process

TABLE 5

Composition of layer outside of core (500 mg naproxen sodium)

| Ingredient | Mg/Tablet |
|---|---|
| Intra-Granular Ingredients | |
| Naproxen Sodium, USP | 500.0 |
| Microcrystalline Cellulose, NF | 52.95 |
| Povidone, USP | 23.60 |
| Purified Water, USP[1] | |
| Extra-Granular Ingredients | |
| Microcrystalline Cellulose, NF | 52.95 |
| Croscarmellose Sodium, NF | 13.50 |
| Talc, USP | 27.0 |
| Magnesium Stearate, NF | 5.0 |
| Total | 675.0 |

[1]Purified Water, USP is removed during the drying process

The intra-granular ingredients from Table 4 (sumatriptan succinate) are charged into high shear granulator (i.e., Gral, PMA). The ingredients are dry mixed and a granulating solution (purified water) is then added while continuously mixing.

Mixing is continued until a desired granulation is achieved. The wet granules are removed from the high shear granulator and are dried in a fluid bed dryer (i.e., Glatt) to achieve a moisture of <1%. The dried granulation is milled using a suitable mill (i.e., Quadro Comil, Fitzmill). The milled granulation and extra-granular ingredients from Table 4 are then added to a blender (e.g., V-Blender, tote blender) and blended until uniform. Magnesium stearate is then added and blended. The blend is discharged into containers (e.g., drums).

Similarly, the intra-granular ingredients from Table 5 (naproxen sodium) are charged into a high shear granulator (e.g., Gral, PMA) and dry mixed. Granulating solution (purified water) is then added while continuously mixing to a desired granulation. The wet granules are removed from the high shear granulator and dried in a fluid bed dryer to achieve a moisture of 1-5%. The dried granulation is milled using a suitable mill (e.g., Quadro Comil, Fitzmill). The milled granulation and extra-granular ingredients from Table 5 are then added to a blender (e.g., V-Blender, tote blender) and blended until uniform. Lubricants, magnesium stearate and talc, are then added and blended. The blend is discharged into suitable containers (e.g., drums).

Tablets are compressed using a compression-coated tablet press (e.g., Manesty Drycota) with the blend of ingredients in Table 4 as the core or inner layer and ingredients in Table 5 outside the core in an outer layer. The tablets can be film coated in a coating pan (e.g., Accela Cota) for aesthetic purposes.

Example 2

Opioid Analgesic and NSAID

Figure 2:
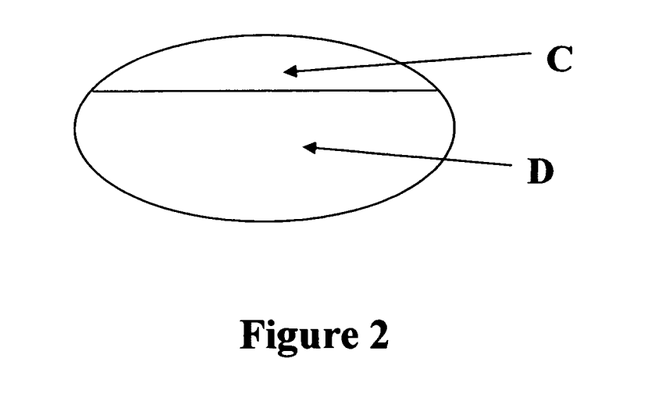
FIG. 2 shows a bilayer tablet configuration in which an absorption-impairing drug is in one layer and a drug that does not impair absorption is in the other layer. C: Drug in Layer 1; D: Drug in Layer 2.
Figure 5:
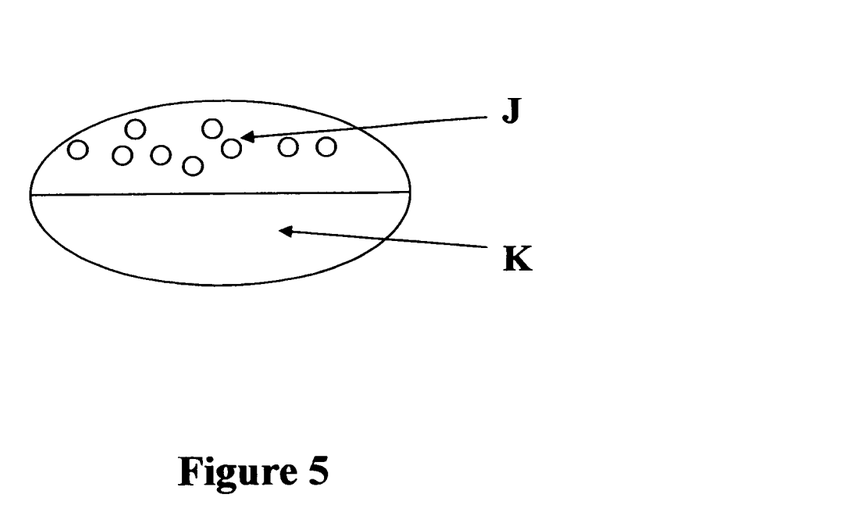
FIG. 5 shows a bilayer tablet configuration in which an absorption impairing drug is in coated pellets in one layer and a drug that does not impair absorption is in the other layer. J: Drug in Pellets in Layer 1; K: Drug in Layer 2.

This example describes a bilayer tablet consisting of sustained release hydrocodone and naproxen sodium. Refer to FIG. 2 for a schematic of the tablet or FIG. 5 for tablet containing pellets.

TABLE 6

| Composition for Layer One (10 mg hydrocodone bitartrate) | |
|---|---|
| Ingredient | Mg/Tablet |
| Intra-Granular Ingredients | |
| Hydrocodone Bitartrate, USP | 10.0 |
| Microcrystalline Cellulose, NF | 37.5 |
| Povidone, USP | 15.0 |
| Hydroxypropyl methylcellulose (Methocel K4M) | 45.0 |
| Purified Water, USP[1] | QS |
| Extra-Granular Ingredients | |
| Microcrystalline Cellulose, NF | 45.0 |
| Magnesium Stearate, NF | 1.5 |
| Total | 154.0 |

[1]Purified Water, USP is removed during the drying process

TABLE 7

| Composition for Layer 2 (400 mg naproxen sodium) | |
|---|---|
| Ingredient | Mg/Tablet |
| Intra-Granular Ingredients | |
| Naproxen Sodium, USP | 400.0 |
| Microcrystalline Cellulose, NF | 42.2 |

TABLE 7-continued

| Composition for Layer 2 (400 mg naproxen sodium) | |
|---|---|
| Ingredient | Mg/Tablet |
| Povidone, USP | 18.9 |
| Purified Water, USP[1] | QS |
| Extra-Granular Ingredients | |
| Microcrystalline Cellulose, NF | 42.2 |
| Croscarmellose Sodium, NF | 10.8 |
| Talc, USP | 21.6 |
| Magnesium Stearate, NF | 4.0 |
| Total | 540.0 |

[1]Purified Water, USP is removed during the drying process

The intra-granular ingredients from Table 6 (hydrocodone bitartrate) are charged into a high shear granulator (e.g., Gral, PMA) and dry mixed. Granulating solution (purified water) is then added while continuously mixing. Mixing is continued until a suitable granulation is achieved. The wet granules are then removed from the high shear granulator and dried in a fluid bed dryer (e.g., Glatt) to achieve a moisture of 1-5%. The dried granulation is milled using a mill (e.g., Quadro Comil, Fitzmill). The milled granulation and extra-granular ingredients from Table 6 are then added to a blender (e.g., V-Blender, tote blender) and blended until uniform. Magnesium stearate is then added and blended. The blend is discharged into suitable containers (e.g., drums). Alternatively, pellets are produced using a rotary processor for the processes of extrusion, spheronization and drying. The intra-granular ingredients listed in Table 6 including hydrocodone bitartrate, microcrystalline cellulose, povidone and purified water are formed into pellets. These pellets are then film coated with Surelease which is an aqueous dispersion of ethylcellulose and plasticizers. The pellets and the extra-granular ingredients from Table 6 are then added to a blender and blended until uniform.

Similarly, the intra-granular ingredients from Table 7 (naproxen sodium) are charged into a high shear granulator (e.g., Gral, PMA) and dry mixed. Granulating solution (purified water) is then added while continuously mixing. Mixing is continued until a suitable granulation is achieved. The wet granules are removed from the high shear granulator and dried in a fluid bed dryer to achieve a moisture of 1-5%. The dried granulation is milled using a suitable mill (e.g., Quadro Comil, Fitzmill). The milled granulation and extra-granular ingredients from Table 7 are then added to a blender (e.g., V-Blender, tote blender) and blended until uniform. Lubricants, magnesium stearate and talc, are then added and blended. The blend is discharged into suitable containers (e.g., drums).

Tablets are compressed into bilayer tablets using a multi-layered tablet press (e.g., Courtoy, Stokes) with blend (or blend containing pellets) from ingredients in Table 6 and ingredients in Table 7. A barrier layer, consisting of an 80:20 mixture of anhydrous lactose, NF and microcrystalline cellulose, NF may be included between the hydrocodone bitartrate and naproxen sodium layers so that a trilayer tablet is compressed. The tablets may be film coated for aesthetic purposes.

Example 3

Opioid Analgesic and NSAID

Figure 3:
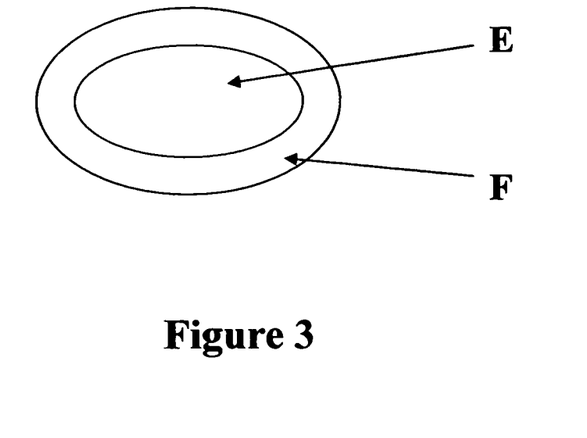
FIG. 3: The figure shows a tablet arrangement in which there is a core that contains an absorption-impairing drug and this core is surrounded by a film coating containing a drug that does not impair absorption. E: Drug in Core; F: Drug in Film Coat.

The present example describes a hydrocodone core tablet with lomoxicam in a filmcoat. Refer to FIG. 3 for a schematic of the tablet.

TABLE 8

Composition for core tablet (10 mg hydrocodone bitartrate)

| Ingredient | Mg/Tablet |
| --- | --- |
| Intra-Granular Ingredients | |
| Hydrocodone Bitartrate, USP | 10.0 |
| Microcrystalline Cellulose, NF | 35.0 |
| Anhydrous Lactose, NF | 103.0 |
| Povidone, USP | 8.0 |
| Purified Water, USP[1] | QS |
| Extra-Granular Ingredients | |
| Microcrystalline Cellulose, NF | 35.0 |
| Croscarmellose Sodium, NF | 8.0 |
| Magnesium Stearate, NF | 1.0 |
| Total | 200 |

[1]Purified Water, USP is removed during the drying process

TABLE 9

Composition of film coat containing lornoxicam

| Ingredient | Mg/Tablet |
| --- | --- |
| Active Film Coat | |
| Opadry Clear | 30.0 |
| Piroxicam | 20.0 |
| Polysorbate 80, NF | 2.0 |
| Sodium Phosphate Dibasic Anhydrous, USP | 1.0 |
| Purified Water, USP[1] | QS |
| Color Film Coat | |
| Opadry White | 10.0 |
| Purified Water, USP[1] | QS |

[1]Purified Water, USP is removed during the film coating process.

The intragranular ingredients from Table 8 (hydrocodone bitartrate) are charged into a high shear granulator (e.g., Gral, PMA) and dry mixed. Granulating solution (purified water) is then added while continuously mixing. Mixing is continued until the desired granulation is achieved. The wet granules are removed from the high shear granulator and dried in a fluid bed dryer (e.g., Glatt) to achieve a moisture of 1-5%. The dried granulation is milled using a suitable mill (e.g., Quadro Comil, Fitzmill). The milled granulation and extra-granular ingredients from Table 8 are then added to a blender (e.g., V-Blender, tote blender) and blended until uniform. Magnesium stearate is then added and blended. The blend is discharged into suitable containers (e.g., drums). Tablets are compressed from the blend on a tablet press.

The active coating suspension (Table 9) is prepared by mixing polysorbate 80, sodium phosphate buffer, and lornoxicam. Purified water is added and mixed. Opadry Clear is added to the suspension and mixed. The core tablets are loaded into a coating pan and the active coating suspension is applied to the core tablets. Alternatively, the core tablets may be film coated with a subcoat consisting of Opadry Clear prior to the active film coat. Another alternative is that the core tablets may be film coated with a layer consisting of Surelease which is an aqueous dispersion consisting of ethylcellulose and plasticizers. A white coating suspension is prepared by combining Opadry White and purified water and mixing until dispersed. The white coating suspension is then applied to the tablets.

Example 4

Opioid analgesic and NSAID

Figure 4:
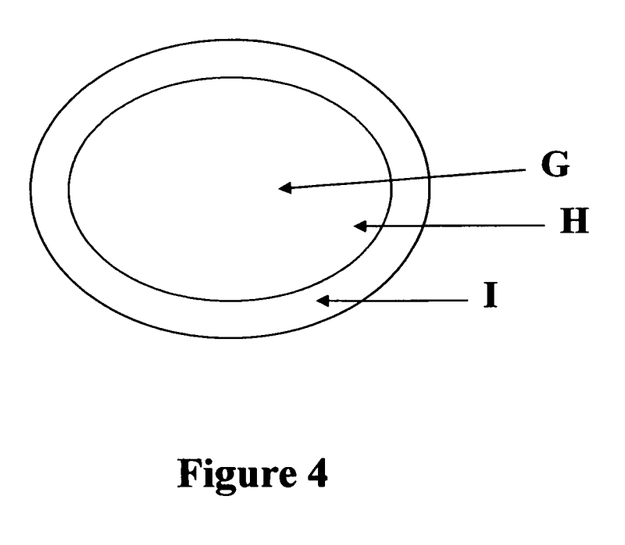
FIG. 4 shows a tablet with a core which contains an absorption-impairing drug and which is surrounded by an enteric coating. In addition, there is an outer layer that surrounds the enteric coated core and which contains a drug that does not impair absorption. G: Drug in Core; H: Enteric or Controlled Release Film Coat; I: Drug in Film Coat.

Example 4 is a delayed release hydrocodone tablet with lornoxicam in film coat. Refer to FIG. 4 for a schematic of the tablet.

TABLE 10

Enteric Film Coat

| Ingredient | Mg/Tablet |
| --- | --- |
| Methacrylic Acid Copolymer Dispersion, NF (Eudragit L30D-55) | 24.9 |
| Triethyl Citrate, NF | 3.7 |
| Glyceryl Monostearate, NF | 1.0 |
| Polysorbate 80, NF | 0.4 |
| Purified Water, USP[1] | QS |

[1]Purified Water, USP is removed during the film coating process

The core tablet described in Example 3 is film coated with an enteric film coat. The ingredients for the enteric coat are listed in Table 10. Glyceryl monostearate is melted in purified water at approx. 60° C. Polysorbate 80 is added and the mixture is cooled to room temperature. Triethyl citrate is added to the methacrylic acid copolymer dispersion and mixed. The glyceryl monostearate dispersion is added to the methacrylic acid copolymer dispersion and mixed until uniform. The resultant dispersion is applied to the core tablets in a coating pan. The active film coat and white color coat described in Table 9 are then applied to the tablets.

Example 5

Opioid analgesic and NSAID

Example 5 is a controlled release hydrocodone tablet with lornoxicam in film coat. Refer to FIG. 4 for a schematic of the tablet.

TABLE 11

Controlled Release Film Coat

| Ingredient | Mg/Tablet |
| --- | --- |
| Surelease | 20.0 |
| Purified Water, USP[1] | QS |

[1]Purified Water, USP is removed during the film coating process

The core tablet described in Example 3 is film coated with a film coat containing Surelease as shown in Table 11. Surelease is supplied by Colorcon as a 25% w/w aqueous dispersion containing ethylcellulose and plasticizers. Surelease is mixed with additional purified water as appropriate and the resultant dispersion is applied to the core tablets in a coating pan. The active film coat and white color coat described in Table 9 are then applied to the tablets.

Example 6

Triptan and NSAID Using Bicarbonate in the NSAID Layer to Speed Absorption

The present example describes a compression-coated or press-coated tablet consisting of sumatriptan succinate in the core and naproxen sodium surrounding the core. Refer to FIG. 1 for schematic of the tablet.

TABLE 12

Composition for Core (40 mg sumatriptan)

| Ingredient | Mg/Tablet |
| --- | --- |
| Intra-Granular Ingredients | |
| Sumatriptan Succinate, USP[1] | 56.0 |
| Lactose Monohydrate, NF | 56.0 |
| Purified Water, USP[2] | QS |
| Extra-Granular Ingredients | |
| Anhydrous Lactose, NF | 112.0 |
| Microcrystalline Cellulose, NF | 26.2 |
| Croscarmellose Sodium, NF | 2.54 |
| Magnesium Stearate, NF | 1.27 |
| Total | 254.0 |

[1]56.0 mg of sumatriptan succinate is equivalent to 40 mg of sumatriptan
[2]Purified Water, USP is removed during the drying process

TABLE 13

Composition of layer outside of core (500 mg naproxen sodium)

| Ingredient | Mg/Tablet |
| --- | --- |
| Intra-Granular Ingredients | |
| Naproxen Sodium, USP | 500.0 |
| Microcrystalline Cellulose, NF | 64.0 |
| Povidone, USP | 28.0 |
| Purified Water, USP[1] | |
| Extra-Granular Ingredients | |
| Sodium Bicarbonate, USP | 90.0 |
| Microcrystalline Cellulose, NF | 64.0 |
| Croscarmellose Sodium, NF | 16.0 |
| Talc, USP | 32.0 |
| Magnesium Stearate, NF | 6.0 |
| Total | 800.0 |

[1]Purified Water, USP is removed during the drying process

The intra-granular ingredients from Table 12 (sumatriptan succinate) are charged into high shear granulator (i.e., Gral, PMA). The ingredients are dry mixed and a granulating solution (purified water) is then added while continuously mixing. Mixing is continued until a desired granulation is achieved. The wet granules are removed from the high shear granulator and are dried in a fluid bed dryer (i.e., Glatt) to achieve a moisture of <1%. The dried granulation is milled using a suitable mill (i.e., Quadro Comil, Fitzmill). The milled granulation and extra-granular ingredients from Table 12 are then added to a blender (e.g., V-Blender, tote blender) and blended until uniform. Magnesium stearate is then added and blended. The blend is discharged into containers (e.g., drums).

Similarly, the intra-granular ingredients from Table 13 (naproxen sodium) are charged into a high shear granulator (e.g., Gral, PMA) and dry mixed. Granulating solution (purified water) is then added while continuously mixing to a desired granulation. The wet granules are removed from the high shear granulator and dried in a fluid bed dryer to achieve a moisture of 1-5%. The dried granulation is milled using a suitable mill (e.g., Quadro Comil, Fitzmill). The milled granulation and extra-granular ingredients from Table 13 are then added to a blender (e.g., V-Blender, tote blender) and blended until uniform. Lubricants, magnesium stearate and talc, are then added and blended. The blend is discharged into suitable containers (e.g., drums).

Tablets are compressed using a compression-coated tablet press (e.g., Manesty Drycota) with the blend of ingredients in Table 12 as the core or inner layer and ingredients in Table 13 outside the core in an outer layer. The tablets can be film coated in a coating pan (e.g., Accela Cota) for aesthetic purposes.

Example 7

Opioid Analgesic and NSAID Using Bicarbonate in the NSAID Layer to Speed Absorption This example describes a bilayer tablet consisting of sustained release hydrocodone and naproxen sodium. Refer to FIG. 2 for a schematic of the tablet or FIG. 5 for tablet containing pellets.

TABLE 14

Composition for Layer One (10 mg hydrocodone bitartrate)

| Ingredient | Mg/Tablet |
| --- | --- |
| Intra-Granular Ingredients | |
| Hydrocodone Bitartrate, USP | 10.0 |
| Microcrystalline Cellulose, NF | 37.5 |
| Povidone, USP | 15.0 |
| Hydroxypropyl methylcellulose (Methocel K4M) | 45.0 |
| Purified Water, USP[1] | QS |
| Extra-Granular Ingredients | |
| Microcrystalline Cellulose, NF | 45.0 |
| Magnesium Stearate, NF | 1.5 |
| Total | 154.0 |

[1]Purified Water, USP is removed during the drying process

TABLE 15

Composition for Layer 2 (400 mg naproxen sodium)

| Ingredient | Mg/Tablet |
| --- | --- |
| Intra-Granular Ingredients | |
| Naproxen Sodium, USP | 400.0 |
| Microcrystalline Cellulose, NF | 52.3 |
| Povidone, USP | 23.6 |
| Purified Water, USP[1] | QS |
| Extra-Granular Ingredients | |
| Sodium Bicarbonate, USP | 101.3 |
| Microcrystalline Cellulose, NF | 52.3 |
| Croscarmellose Sodium, NF | 13.5 |
| Talc, USP | 27.0 |
| Magnesium Stearate, NF | 5.0 |
| Total | 675.0 |

[1]Purified Water, USP is removed during the drying process

The intra-granular ingredients from Table 14 (hydrocodone bitartrate) are charged into a high shear granulator (e.g., Gral, PMA) and dry mixed. Granulating solution (purified water) is then added while continuously mixing. Mixing is continued until a suitable granulation is achieved. The wet granules are then removed from the high shear granulator and dried in a fluid bed dryer (e.g., Glatt) to achieve a moisture of 1-5%. The dried granulation is milled using a mill (e.g., Quadro Comil, Fitzmill). The milled granulation and extra-granular ingredients from Table 14 are then added to a blender (e.g., V-Blender, tote blender) and blended until uniform. Magnesium stearate is then added and blended. The blend is discharged into suitable containers (e.g., drums). Alternatively, pellets are produced using a rotary processor for the processes of extrusion, spheronization and drying. The intra-granular ingredients listed in Table 14 including hydrocodone bitartrate, microcrystalline cellulose, povidone and purified water are formed into pellets. These pellets are then film coated with Surelease which is an aqueous dispersion of ethylcellulose and plasticizers. The pellets and the extra-granular ingredients from Table 14 are then added to a blender and blended until uniform.

Similarly, the intra-granular ingredients from Table 15 (naproxen sodium) are charged into a high shear granulator (e.g., Gral, PMA) and dry mixed. Granulating solution (purified water) is then added while continuously mixing. Mixing is continued until a suitable granulation is achieved. The wet granules are removed from the high shear granulator and dried in a fluid bed dryer to achieve a moisture of 1-5%. The dried granulation is milled using a suitable mill (e.g., Quadro Comil, Fitzmill). The milled granulation and extra-granular ingredients from Table 15 are then added to a blender (e.g., V-Blender, tote blender) and blended until uniform. Lubricants, magnesium stearate and talc, are then added and blended. The blend is discharged into suitable containers (e.g., drums).

Tablets are compressed into bilayer tablets using a multi-layered tablet press (e.g., Courtoy, Stokes) with blend (or blend containing pellets) from ingredients in Table 14 and ingredients in Table 15. A barrier layer, consisting of an 80:20 mixture of anhydrous lactose, NF and microcrystalline cellulose, NF may be included between the hydrocodone bitartrate and naproxen sodium layers so that a trilayer tablet is compressed. The tablets may be film coated for aesthetic purposes.

All references cited herein are fully incorporated by reference. Having now fully described the invention, it will be understood by those of skill in the art that the invention may be practiced within a wide and equivalent range of conditions, parameters and the like, without affecting the spirit or scope of the invention or any embodiment thereof.

What is claimed is:

1. A pharmaceutical composition in unit dosage form for oral administration, comprising:
   a) a therapeutically effective amount of a first drug, wherein said first drug is an opioid analgesic that impairs the absorption of medication from the gastrointestinal tract of patients and essentially all of said first drug is either surrounded by a membrane that delays its release after ingestion or is formulated with components that delay its release after ingestion; and
   b) a therapeutically effective amount of a second drug, wherein said second drug does not impair the absorption of medication from the gastrointestinal tract of patients; and wherein, upon ingestion of said unit dosage form by a patient,
   i) said second drug is released from said unit dosage form into the gastrointestinal tract of said patient before said first drug; and
   ii) said first drug is not released from said unit dosage form for a period of time equal to at least one-fourth Tmax2, wherein Tmax2 is the time needed for said second drug to reach peak plasma concentration when said second drug is administered to a patient as the sole active agent.

2. The pharmaceutical composition of claim 1, wherein said unit dosage form is a multilayer tablet.

3. The pharmaceutical composition of claim 2, wherein the release of said first drug is delayed for a minimum of 15 minutes after ingestion and said second drug is released from said dosage from within 5 minutes after ingestion.

4. The pharmaceutical composition of claim 3, wherein:
   (a) essentially all of said first drug is in a single core layer; and
   (b) essentially all of said second drug is located in one or more layers outside of said core layer that include a disintegrant or a compound that causes effervescence.

5. The pharmaceutical composition of claim 1, wherein said dosage form is a capsule.

6. The pharmaceutical composition of claim 5, wherein the release of said first drug is delayed for a minimum of 15 minutes after ingestion and said second drug is released from said dosage from within 5 minutes after ingestion.

7. The pharmaceutical composition of claim 6, wherein:
   (a) said capsule comprises multiple particles of said first drug; and
   (b) essentially all of said second drug is located outside of said particles together with a disintegrant or a compound that causes effervescence.

8. The pharmaceutical composition of claim 1, wherein said opioid analgesic is selected from the group consisting of: algentanil; buprenophine; butorphanol; codeine; dezocine; dihydrocodeine; fentanyl; hydrocodone; hydromorphone; levorphanol; meperidine; methadone; morphine; nalbuphine; oxycodone; oxymorphone; pentazocine; propiram; propoxyphene; sufentanil; and tramadol.

9. The pharmaceutical composition of claim 8, wherein said second drug is either acetaminophen or an NSAID selected from the group consisting of: naproxen; ibuprofen; flurbiprofen; ketoprofen; oxaprozin; etodolac; ketorolac; nabumetone; mefenamic acid; indomethacin; piroxicam; celecoxib; and rofecoxib.

10. A method of treating a patient for pain comprising administering to said patient a therapeutically effective amount of the pharmaceutical composition of claim 1.

11. The pharmaceutical composition of claim 1, wherein said unit dosage form is a multilayer tablet, said second drug is an NSAID and the release of said first drug is delayed for a minimum of 10 minutes.

12. The pharmaceutical composition of claim 11, wherein the release of said first drug is delayed for a minimum of 20 minutes.

13. The pharmaceutical composition of claim 11, wherein the release of said first drug is delayed for a minimum of 30 minutes.

14. The pharmaceutical composition of claim 11, wherein the release of said first drug is delayed for a minimum of 60 minutes.

15. The pharmaceutical composition of claim 11, wherein:
   a) essentially all of said first drug is in a single core layer; and
   b) essentially all of said second drug is located in one or more layers outside of said core layer that include a disintegrant or a compound that causes effervescence.

16. The pharmaceutical composition of claim 15, wherein said opioid analgesic is selected from the group consisting of: alfentanil; buprenorphine; butorphanol; codeine; dezocine; dihydrocodeine; fentanyl; hydrocodone; hydromorphone; levorphanol; meperidine; methadone; morphine; nalbuphine; oxycodone; oxymorphone; pentazocine; propiram; propoxyphene; sufentanil; and tramadol.

17. The pharmaceutical composition of claim 16, wherein said opioid analgesic is either fentanyl or tramadol.

18. The pharmaceutical composition of claim 16, wherein said NSAID is ibuprofen.

19. The pharmaceutical composition of claim 16, wherein said NSAID is enteric coated.

20. The pharmaceutical composition of claim 16, wherein said single core layer comprises a disintegrant.

21. The pharmaceutical formulation of claim 1, wherein:
a) the release of said first drug from said unit dosage form is delayed for at least 20 minutes after said dosage form is ingested; and
b) said second drug is selected from the group consisting of acetaminophen and an NSAID and is released from said unit dosage form into the gastrointestinal tract of said patient within 5 minutes after said dosage form is ingested.

\* \* \* \* \*